United States Patent [19]
McFarland et al.

[11] 4,009,160
[45] Feb. 22, 1977

[54] AMINOMETHYLARYLMETHYLPENICIL-LIN DERIVATIVES
[75] Inventors: James W. McFarland, Lyme; Colin Thomson, Groton, both of Conn.
[73] Assignee: Pfizer Inc., New York, N.Y.
[22] Filed: Feb. 17, 1976
[21] Appl. No.: 658,489

Related U.S. Application Data
[62] Division of Ser. No. 523,024, Nov. 12, 1974, Pat. No. 3,966,710.
[52] U.S. Cl. .............................. 260/239.1
[51] Int. Cl.$^2$ ................................ C07D 499/58
[58] Field of Search ........................ 260/239.1

[56] References Cited
FOREIGN PATENTS OR APPLICATIONS
1,057,029  2/1967  United Kingdom ............ 260/239.1

Primary Examiner—Gerald A. Schwartz
Attorney, Agent, or Firm—Connolly and Hutz

[57] ABSTRACT
6-(Aminomethyl substituted phenyl- and thienylacetamido)penicillanic acid and esters, and synthetic methods for the preparation thereof.

6 Claims, No Drawings

AMINOMETHYLARYLMETHYLPENICILLIN DERIVATIVES

CROSS-REFERENCE TO RELATED APPLICATION

This application is a divisional of application Ser. No. 523,024 filed Nov. 12, 1974, now U.S. Pat. No. 3,966,710.

BACKGROUND OF THE INVENTION

1. Field of the Invention

This invention relates to a series of penicillins and in particular to 6-(phenyl- and thienylacetamido)penicillanic acid and esters which are substituted in the phenyl and thienyl moieties with an aminomethyl substituent, possessing high antibacterial activity, especially against such gram-negative microorganisms as *E. coli* and *Klebsiella*.

2. Description of the Prior Art

The compounds belonging to the family of penicillins differ from each other in the nature of the R variable and possess the general formula indicated below wherein the acyl moiety on the 6-aminopenicillanic acid

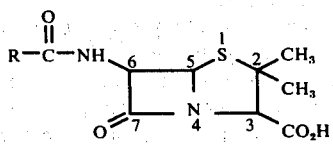

is derived from a carboxylic acid or functional derivative thereof such as an acyl halide or anhydride.

The pharmacodynamic properties and antibiotic profile of a given penicillin are determined to a large extent by the nature of the R group. The most widely used penicillins are those wherein the R moiety is represented by benzyl-, phenoxymethyl- or α-phenoxyethyl-. While these well-known analogs are highly antagonistic toward gram-positive microorganisms they have limited gram-negative activity. Consequently, drugs which will combat a rise in gram-negative infections, e.g., *E. coli*, Pseudomonas or Klebsiella, are of value to the medical profession.

Recent efforts to improve the profile of activity within the family of penicillins have resulted in the synthesis of several new agents. 6-(p-aminomethylphenylacetamido)penicillanic acid is claimed in British Pat. No. 1,057,029, while 6-(o-, m- and p-aminomethylphenoxyacetamido)penicillanic acids are described by Schorr, et al., *Arch. Pharmaz.*, 304, 325 (1971). Aminomethyl substituted 7-(phenyl-, phenylthio- and phenoxyacetamido)cephalosporanic acid derivatives are described in U.S. Pat. Nos. 3,766,175; 3,766,176; 3,813,376; 3,813,390 and 3,813,391.

SUMMARY OF THE INVENTION

It has now been found that certain 6-(aminomethyl substituted phenyl- and thienylacetamido)penicillanic acids and esters thereof and their pharmaceutically acceptable salts are outstandingly active against a broad spectrum of microorganisms, especially gram-negative microorganisms.

A preferred group of compounds and their pharmaceutically acceptable salts are those of the formula

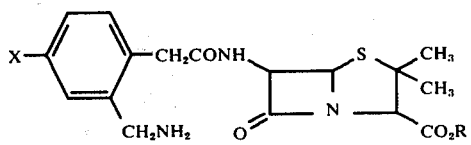

wherein X is hydrogen or hydroxy and R is hydrogen, 1-(alkanoyloxy)alkyl said alkanoyl having 2 to 8 carbon atoms and said alkyl having 1 to 3 carbon atoms or phthalidyl. Within this first preferred group are particularly preferred those congeners where R is hydrogen, said 1-(alkanoyloxy)alkyl and phthalidyl.

A second preferred class of penicillanic acid derivatives and their pharmaceutically acceptable salts are of the formulae

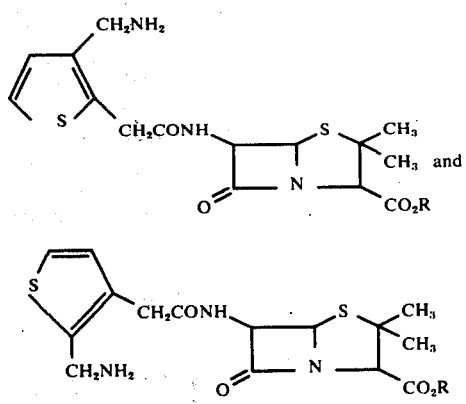

where R is hydrogen, 1-(alkanoyloxy)alkyl said alkanoyl having 2 to 8 carbon atoms and said alkyl having 1 to 3 carbon atoms or phthalidyl. Particularly preferred within said second group of preferred compounds are those wherein R is said 1-(alkanoyloxy)alkyl, hydrogen or phthalidyl.

DETAILED DESCRIPTION OF THE INVENTION

In accordance with the process employed for synthesizing the penicillins of the present invention, the following reaction scheme is illustrative:

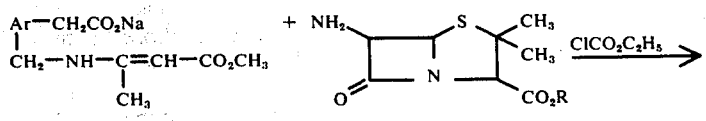

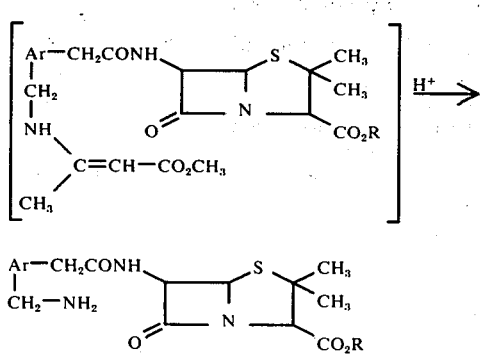

Ar—CH$_2$CONH — [β-lactam-thiazolidine] — CO$_2$R
|
CH$_2$—NH$_2$ wherein R is as previously indicated, and Ar is 1,2-phenylene, 4-hydroxy-1,2-phenylene or 2,3-thienylene.

In practice, the appropriate sodium 1-methoxycarbonyl-1-propen-2-ylaminomethyl substituted arylacetate is converted in situ to a mixed anhydride by reacting said arylacetate with an equimolar amount of ethyl chloroformate and a tertiary amine, such as triethylamine or N-methylmorpholine, in an aprotic reaction-inert solvent, such as ethyl acetate or tetrahydrofuran. In order to minimize decomposition of the mixed anhydride, it is preferred that its formation be carried out at a temperature of about −15° C.

When formation of the anhydride is complete, which requires 30–45 minutes, an equimolar amount of 6-aminopenicillanic acid in a solution of water-tetrahydrofuran is added, and the pH adjusted to 7 by the addition of 1N aqueous sodium hydroxide. When employing those derivatives of 6-aminopenicillanic acid wherein R is 1-(alkanoyloxy)alkyl or phthalidyl, it is preferred that said derivative be added to the mixed anhydride without benefit of water and without adjustment of the pH with aqueous base.

After 30–60 minutes at room temperature, the reaction of the mixed anhydride with 6-aminopenicillanic acid or its derivatives is complete and the organic solvent is removed in vacuo. The 1-methoxycarbonyl-1-propen-2-yl moiety on the aminomethyl substituent is conveniently removed by acid hydrolysis, which comprises stirring an aqueous suspension of the intermediate to which sufficient 3N hydrochloric acid has been added to give a pH 1.5. The hydrolysis is best achieved at ice-bath temperature for a period of 30–40 minutes.

Isolation of those products wherein R is hydrogen is best achieved by adding sufficient aqueous sodium hydroxide to reach the isoelectric point of the final product, or approximately pH 5.5 Storage in the cold (10° C.) results in the formation of the precipitated product. After filtration of the product, additional material can be isolated by concentration of the filtrate and cooling.

Isolation of those products wherein R is 1-(alkanoyloxy)alkyl or phthalidyl is achieved by filtering the relatively insoluble hydrochloride salt resulting from the above described hydrolysis. The free base can be isolated by treating an aqueous solution or suspension with an equimolar amount of a suitable water soluble base, such as sodium or potassium hydroxide.

The starting materials for the aforedescribed reactions are easily prepared by methods familiar to those skilled in the art. The 2-aminomethylphenylacetic acids are synthesized by the procedure as described in U.S. Pat. Nos. 3,796,716 and/or 3,796,717. Blockage of the amino group with a β-keto ester is taught in Japan 71/24714 and U.S. Pat. No. 3,813,376. While 6-aminopenicillanic acid is a commercial product, the corresponding 1-(alkanoyloxy)alkyl or phthalidyl ester can be synthesized by the procedures as taught by Daehne, et al., J. Med. Chem., 13, 607 (1970) and in German Pat. No. 2,225,149, respectively.

As has been previously noted, a characteristic feature of the acidic compounds of the instant invention wherein R is hydrogen is their ability to form basic salts. Acid congeners of the present invention are converted to basic salts by the interaction of said acid with an appropriate base in an aqueous or nonaqueous medium. Such basic reagents suitably employed in the preparation of said salts can vary in nature, and are meant to contemplate such bases as organic amines, ammonia, alkali metal hydroxides, carbonates, bicarbonates, hydrides, alkanoates and alkoxides, as well as alkali earth metal hydroxides, hydrides, alkoxides and carbonates. Representative of such bases are ammonia, primary amines such as n-propylamine, n-butylamine, aniline, cyclohexylamine, p-toluidine, ethylamine, octylamine, secondary amines such as dicyclohexylamine and tertiary amines such as diethylaniline, N-methylpyrrolidine, N-methylmorpholine and 1,5-diazabicyclo[4,3,0]-nonene; sodium hydroxide, potassium hydroxide, ammonium hydroxide, sodium ethoxide, potassium methoxide, magnesium hydroxide, potassium and sodium 2-ethylhexanoates, calcium hydride and barium hydroxide.

In the utilization of the chemotherapeutic activity of those compounds of the present invention which form basic salts, it is preferred, of course, to use pharmaceutically acceptable salts. Although water insolubility, high toxicity, or lack of crystalline nature may make some salt species unsuitable or less desirable for use as such in a given pharmaceutical application, the water insoluble or toxic salts can be converted to the corresponding acids by decomposition of the salts, or alternately they can be converted to any desired pharmaceutically acceptable basic salt. The said pharmaceutically acceptable salts preferred include the sodium, aluminum, potassium, calcium, magnesium, ammonium and sustituted ammonium salts, e.g. procaine, dibenzylamine, N,N-bis(dehydroabietyl)ethylenediamine, 1-ephenamine, N-ethylpiperidine, N-benzyl-β-phenethylamine, N,N'-dibenzylethylenediamine, triethylamine, as well as salts with other amines which have been used to form salts with benzylpenicillin.

As has been previously noted, compounds of the instant invention can form acid addition salts by virtue of the amino group of the aminomethyl substituent.

Basic compounds of the present invention are converted to the acid addition salts by interaction of the base with an acid either in an aqueous or non-aqueous medium. In a similar manner, treatment of the acid addition salts with an aqueous base solution, e.g., alkali metal hydroxides, alkali metal carbonates, and alkali metal bicarbonates to a basic pH or to the isoelectric point (where R = H), or with a metal cation which forms an insoluble precipitate with the acid anion, results in a regeneration of the free base form. Such conversions are best carried out as rapidly as possible and under temperature conditions and method dictated by the stability of said basic products. The bases thus regenerated may be reconverted to the same or a different acid additions salt.

In the utilization of the chemotherapeutic activity of those compounds of the present invention which form acid addition salts, it is preferred, of course, to use pharmaceutically acceptable salts. Although water-insolutility, high toxicity, or lack of crystalline nature may make some particular salt species unsuitable or less desirable for use as such in a given pharmaceutical application, the water-insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic and gluconic.

The novel penicillins described herein exhibit in vitro activity against a wide variety of microorganisms, including both gram-positive and gram-negative bacteria. Their useful activity can readily be demonstrated by in vitro tests against various organisms in a brain-heart infusion medium by the usual two-fold serial dilution technique. The in vitro activity of the herein described compounds renders them useful for topical application in the form of ointments, creams and the like, or for sterilization purposes, e.g., sick-room utensils.

These novel penicillins are also effective antibacterial agents in vivo in animals, including man, not only via the parenteral route of administration but also by the oral route of administration.

Obviously, the physician will ultimately determine the dosage which will be most suitable for a particular individual person, and it will vary with the age, weight and response of the particular patient as well as with the nature and extent of the symptoms, the nature of the bacterial infection being treated and the pharmacodynamic characteristics of the particular agent to be administered. It will often be found that when the composition is administered orally, larger quantities of the active ingredient will be required to produce the same level as produced by a lesser quantity administered parenterally.

Having full regard for the foregoing factors it is considered that an effective daily oral dose of the compounds of the present invention in humans of approximately 10–100 mg./kg. per day, with a preferred range of about 25–75 mg./kg. per day in single or divided doses, and a parenteral dose of 10–100 mg./kg. per day, with a preferred range of about 20–75 mg./kg. per day will effectively alleviate the symptoms of the infection. These values are illustrative, and there may, of course, be individual cases where higher or lower dose ranges are merited.

As has been previously mentioned, the penicillins of the present invention are broad spectrum antibiotics which are, unlike many penicillin analogs, highly antagonistic toward gram-negative microorganisms, in particular E. coli and Klebsiella. This unusual activity against certain gram-negative organisms may be attributed to the positioning of the aminomethyl substituent adjacent to the linking amide moiety. The marked effectiveness of this positioning can be readily seen in an antibacterial comparison of 6-(o-aminomethylphenylacetamido)penicillanic acid (o-AMP), a preferred compound of the present invention and 6-(p-aminomethylphenylacetamido)penicillanic acid (p-AMP), a compound of the previously-mentioned British Pat. No. 1,057,029. The tests were conducted under standardized conditions in which nutrient broth containing various concentrations of the test material was seeded with the particular organism specified, and the minimum concentration (MIC) at which growth of each organism failed to occur was observed and recorded.

TABLE I.

In vitro Comparison Data for o-AMP and p-AMP (MIC; mcg./ml.)

| Organism | o-AMP | p-AMP |
|---|---|---|
| S. aureus 01A005 | 0.2 | 200 |
| S. aureus 01A052 | 1.56 | 200 |
| S. pyogenes 020803 | <0.1 | 0.39 |
| E. coli 51A002 | 200 | >200 |
| E. coli 51A215 | 6.25 | 6.25 |
| E. coli 51A266 | 3.12 | 50 |
| Kleb. pneumoniae 53A009 | 3.12 | 50 |
| Salm. typhm. 530013 | 3.12 | 12.5 |
| Past. mult. 59A001 | 0.2 | 0.39 |
| Entero. aero. 55A004 | 1.56 | >200 |

The preferred antibacterial compounds of the present invention are 6-(2-aminomethylphenylacetamido)penicillanic acid; 6-(2-aminomethyl-4-hydroxyphenylacetamido)penicillanic acid; 6-(2-aminomethylphenylacetamido)penicillanic acid, pivaloyloxymethyl ester; 6-(2-aminomethyl-4-hyroxyphenylacetamido)penicillanic acid, pivaloyloxymethyl ester; 6-(2-aminomethylphenylacetamido)penicillanic acid, phthalidyl ester; 6-(2-aminomethyl-4-hydroxyphenylacetamido)penicillanic acid, phthalidyl ester; 6-(2-aminomethyl-3-thienylacetamido)penicillanic acid; 6-(2-aminomethyl-3-thienylacetamido)penicillanic acid, pivaloyloxymethyl ester; 6-(2-aminomethyl-3-thienylacetamido)penicillanic acid, phthalidyl ester; 6-(3-aminomethyl-2-thienylacetamido)penicillanic acid; 6-(3-aminomethyl-2-thienylacetamido)penicillanic acid, pivaloyloxymethyl ester; and 6-(3-aminomethyl-2-thienylacetamido)penicillanic acid, phthalidyl ester.

The novel products of this invention are of value as antibacterial agents and are remarkably effective in treating a number of infections caused by susceptible gram-negative and gram-positive bacteria in poultry and animals including man. For such purposes, the pure materials or mixtures thereof with other antibiotics can be employed. They may be administered alone or in combination with a pharmaceutical carrier on the basis of the chosen route of administration and standard pharmaceutical practice. For example, they may be administered orally in the form of tablets containing such excipients as starch, milk sugar, certain types of clay, etc., or in capsules alone or in admixture with the same or equivalent excipients. They may also be administered orally in the form of elixirs or oral suspensions which may contain flavoring or coloring agents, or be injected parenterally, that is, intramuscularly or subcutaneously. For parenteral administration, they are best used in the form of a sterile aqueous solution which may be either aqueous such as water, isotonic saline, isotonic dextrose, Ringer's solution, or non-aqueous such as fatty oils of vegetable origin (cotton seed, peanut oil, corn, sesame) and other non-aqueous vehicles which will not interfere with the therapeutic efficiency of the preparation and are nontoxic in the volume of proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anesthetics and inorganic salts to afford desirable pharmacological properties.

Further, many of the 1-(alkanoyloxymethyl)alkyl and phthalidyl esters described herein, although inactive or of relatively low activity against gram-negative microorganisms per se are, when administered orally to animals, including man, metabolized to the parent acid, which has a wide spectrum of activity against gram-positive and gram-negative bacteria. They thus serve as pro-drug forms of the parent compounds since they are biologically converted in vivo to said compounds. The rate of metabolic conversion of such esters to the parent acid occurs at such a rate as to provide an effective concentration of the parent acid in the animal body.

The following examples are provided solely for the purpose of illustration and are not to be construed as limitations of this invention, many variations of which are possible without departing from the spirit or scope thereof.

EXAMPLE 1

6-(2-Aminomethylphenylacetamido)penicillanic Acid

To a stirred solution of 42.7 g. (0.149 mole) of sodium 2-(1-methoxy-carbonyl-1-propen-2-ylaminomethyl)phenylacetate in 427 ml. of tetrahydrofuran under a nitrogen atmosphere and cooled to $-15°$ C. is added 42 drops of N-methylmorpholine followed by 16.2 g. (0.149 mole) of ethyl chloroformate. After stirring for 30 min. at $-15°$ C., the reaction mixture is treated with a solution of 31.3 g. (0.149 mole) of 6-aminopenicillanic acid in 168 ml. of water/265 ml. of tetrahydrofuran adjusted to pH 7.4 using 1N aqueous sodium hydroxide. The resulting reaction mixture is allowed to stir at room temperature for 30 min., and the organic solvent subsequently removed in vacuo.

The residual aqueous solution is adjusted to pH 1.5 using 3N hydrochloric acid at 0° C., and allowed to stir for 30 min. The pH is raised to 3.5 with 1N aqueous sodium hydroxide and the aqueous solution is extracted with 500 ml. of ethyl acetate. The water layer is separated and the pH raised further to 5 and the solution stored overnight at approximately 10° C. The first crop of the product is filtered and the filtrate concentrated under reduced pressure to approximately half-volume. Cooling results in the formation of additional precipitate, which is filtered, combined with the first crop and dried, 22.4 g. (42%).

NMR (DMSO-$d_6$-$D_2O$): $\delta$ = 7.40(s) 4H; 5.4(q) 2H; 3.8(s) 2H; 1.66(s) 3H and 1.4(s) 3H. IR (KBr disc):$\gamma\lambda_{max}$ = 1775 cm$^{-1}$ ($\beta$-lactam carbonyl).

EXAMPLE 2

6-(2-aminomethyl-4-hydroxyphenylacetamido)penicillanic acid

Following the acylation procedure of Example 1 and starting with 60.2 g. (0.2 mole) of sodium 2-(1-methoxycarbonyl-1-propen-2-ylaminomethyl)-4-hydroxyphenylacetate, 43.2 g. (0.2 mole) of 6-aminopenicillanic acid, 21.7 g. (0.2 mole) of ethyl chloroformate and 56 drops of N-methylmorpholine, the desired product is isolated in moderate yield.

EXAMPLE 3

6-(2-aminomethylphenylacetamido)penicillanic acid, pivaloyloxymethyl ester hydrochloride To a stirred suspension of 7.79 g. (0.0273 mole) of sodium 2-(1-methoxycarbonyl-1-propen-2-ylaminomethyl)phenylacetate in 60 ml. of ethyl acetate under a nitrogen atmosphere is added 30 drops of N-methylmorpholine, and the reaction mixture cooled in a dry-ice/chloroform bath. To the cooled reaction is added 2.7 g. (0.0273 mole) of ethyl chloroformate and the mixture allowed to stir for 30 min. 6-Aminopenicillanic acid, pivaloyloxymethyl ester (10 g., 0.0273 mole), suspended in 60 ml. of ethyl acetate, is added to the cooled mixture and stirring is continued for 2 hrs.

The reaction mixture is concentrated in vacuo to a yellow semi-solid which is treated with 100 ml. of water and sufficient fresh ethyl acetate to dissolve all the solids. The pH of the cooled (5° C.) solution is adjusted to 1.5 with 3N hydrochloric acid and allowed to stir vigorously for 30 min. The precipitated solid suspended in the two phase system is filtered to give the first crop of product. The organic phase of the two-phase filtrate is separated and the aqueous layer extracted with fresh ethyl acetate (2 × 10 ml.). The organic extracts are combined, dried over sodium sulfate and concentrated under reduced pressure to provide the second crop of product. The crops are combined, triturated with 100 ml. of ethyl acetate and 400 ml. of diethyl ether for 30 min. The product is filtered, washed with ether and dried, 7.55 g. (54%).

NMR (DMSO-$d_6$): $\delta$= 8.5(br) 3H; 7.25(br) 4H; 5.65(q) 2H; 5.40(m) 2H; 4.40(s) 1H; 4.06(s) 2H; 3.73(s) 2H; 1.63(s) 3H; 1.63(s) 3H and 1.16(s) 9H. IR (KBr disc): $\delta_{max}$ = 1790 cm$^{-1}$ ($\beta$-lactam carbonyl).

EXAMPLE 4

Employing the procedure of Example 3 and starting with the appropriate 6-aminopenicillanic acid, 1-(alkanoyloxy)alkyl ester and requisite 2-(1-methoxycarbonyl-1-propen-2-ylaminomethyl)phenylacetate, the following penicillin congeners are synthesized:

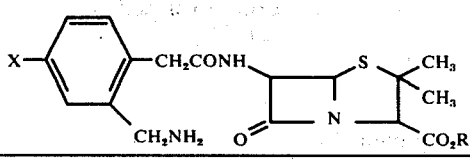

| X   | R                                    |
|-----|--------------------------------------|
| H—  | CH₃CO₂CH₂—                           |
| HO— | CH₃CO₂CH₂—                           |
| H—  | CH₃CO₂CH(CH₃)—                       |
| HO— | CH₃CO₂CH(CH₃)—                       |
| H—  | CH₃CH₂CO₂CH₂—                        |
| H—  | CH₃CH₂CO₂CH(CH₂CH₃)—                 |
| H—  | CH₃CO₂CH(CH₂CH₃)—                    |
| HO— | CH₃CO₂CH(CH₂CH₃)—                    |
| HO— | CH₃(CH₂)₂CO₂CH₂—                     |
| HO— | (CH₃)₂CHCO₂CH₂—                      |
| HO— | CH₃(CH₂)₂CO₂CH(CH₂CH₃)—              |
| H—  | CH₃(CH₂)₂CO₂CH₂—                     |
| HO— | CH₃(CH₂)₃CO₂CH₂—                     |
| H—  | (CH₃)₂CHCH₂CO₂CH(CH₃)—               |
| HO— | (CH₃)₂CHCH₂CO₂CH(CH₃)—               |
| H—  | (CH₃)₃CCO₂CH₂—                       |
| HO— | (CH₃)₃CCO₂CH₂—                       |
| HO— | (CH₃)₃CCO₂CH₂—                       |
| H—  | (CH₃)₃CCO₂CH(CH₂CH₃)—                |
| HO— | (CH₃)₃CCO₂CH(CH₂CH₃)—                |

EXAMPLE 5

6-(2-aminomethylphenylacetamido)penicillanic acid, phthalidyl ester

In a manner similar to Example 3, ethyl chloroformate (3.2 g., 0.03 mole) is added dropwise to a reaction mixture of 8.6 g. (0.03 mole) of sodium 2-(1-methoxycarbonyl-1-propen-2-ylaminomethyl)phenylacetate and 33 drops of N-methylmorpholine in 65 ml. of ethyl acetate under a nitrogen atmosphere and cooled in a dry-ice/chloroform bath. After allowing the mixture to stir in the cold for 30 min., 10.4 g. (0.03 mole) of 6-aminopenicillanic acid, phthalidyl ester in 65 ml. of ethyl acetate is added, and the stirring continued for 2.5 hrs.

Without allowing the mixture to warm to room temperature, the mixture is quenched with 120 ml. of cold water, and the pH adjusted to 1.5 with 6N hydrochloric acid. After stirring for 20 min., the pH is adjusted to 7.5–8.0 with 1N aqueous sodium hydroxide. The organic layer is immediately separated and the aqueous layer subsequently extracted with fresh ethyl acetate (2 × 75 ml.). The original ethyl acetate and extracts are combined, dried over sodium sulfate and concentrated to dryness. The product can be used as isolated, or can be converted to the hydrochloride acid addition salt by treating an ethyl acetate solution of the free base with sufficient hydrogen chloride dissolved in the same solvent to ensure complete precipitation of the hydrochloride salt.

EXAMPLE 6

6-(2-aminomethyl-4-hydroxyphenylacetamido)penicillanc acid, phthalidyl ester

Employing the procedure of Example 5 and starting with 9.98 g. (0.035 mole) of sodium 2-(1-methoxycarbonyl-1-propen-2-ylaminomethyl)-4-hydroxyphenyl acetate, 3.8 g. (0.035 mole) of ethyl chloroformate, 40 drops of N-methylmorpholine and 12.2 g. (0.035 mole) of 6-aminopenicillanic acid, phthalidyl ester, the desired product is prepared.

EXAMPLE 7

6-(2-aminomethyl-3-thienylacetamido)penicillanic acid

Under a nitrogen atmosphere and at dry-ice chloroform temperatures, a solution of 2.91 g. (0.01 mole) of sodium 2-(1-methoxycarbonyl-1-propen-2-ylaminomethyl)-3-thienylacetate and 28 drops of N-methylmorpholine in 28.5 ml. of tetrahydrofuran is treated with 1.08 g. (0.01 mole) of ethyl chloroformate, and the resulting reaction mixture allowed to stir at −15° C. for 30 min. A solution of 2.16 g. (0.01 mole) of 6-aminopenicillanic acid in 12 ml. of water/18 ml. of tetrahydrofuran adjusted to pH 7.4 using 1N aqueous sodium hydroxide is added to the mixture, which is then allowed to stir at room temperature for 30 min.

The organic solvent is removed under reduced pressure and the residual aqueous solution treated at 0° C. with sufficient 3N hydrochloric acid to raise the pH to 1.5. After stirring the solution for 30 min., the pH is adjusted to 3.5 with 1N aqueous sodium hydroxide. The solution is subsequently extracted with ethyl acetate and the aqueous layer separated, the pH raised to 5 with 1N aqueous sodium hydroxide, and concentrated to half volume. After storage overnight at 10°–15° C., the precipitated product is filtered and dried.

EXAMPLE 8

The procedure of Example 7 is repeated, substituting sodium 3-(1-methoxycarbonyl-1-propen-2-ylaminomethyl)-4-thienylacetate for 2-(1-methoxycarbonyl-1-propen-2-ylaminomethyl)-3-thienylacetate to provide the product, 6-(3-aminomethyl-2-thienylacetamido)-penicillanic acid, in moderate yield.

EXAMPLE 9

6-(2-aminomethyl-3-thienylacetamido)penicillanic acid pivaloyloxymethyl ester

Under a nitrogen atmosphere, a stirred suspension of 2.91 g. (0.01 mole) of sodium 2-(1-methoxycarbonyl-1-propen-2-ylaminomethyl)-3-thienylacetate and 10 drops of N-methylmorpholine in 20 ml. of ethyl acetate at dry-ice/chloroform temperatures is treated dropwise with 1.08 g. (0.01 mole) of ethyl chloroformate. After the reaction mixture is allowed to stir for 30 min., 3.66 g. (0.01 mole) of 6-aminopenicillanic acid, pivaloyloxymethyl ester suspended in 10 ml. of ethyl acetate is added, and the stirring continued for an additional 30 min.

The reaction mixture is concentrated under reduced pressure to a semi-solid, which is treated with 35 ml. of water and sufficient ethyl acetate to dissolve the solids. After cooling the two phase system to 0–5° C., the pH is adjusted to 1.5 with 3N hydrochloric acid and the mixture stirred vigorously for 30 min. The precipitated hydrochloride salt of the product which forms in the two phase system is filtered, washed with fresh ethyl acetate/diethyl ether and dried.

The free base is liberated by suspending the salt in 100 ml. water/100 ml. ethyl acetate followed by cooling and the addition of sufficient 1N aqueous sodium hydroxide to give a pH of 8–8.5. The ethyl acetate layer is separated, and the aqueous layer further extracted with fresh solvent (2 × 50 ml.). The combined ethyl acetate extracts are dried over sodium sulfate and concentrated to provide the desired product.

EXAMPLE 10

6-(3-aminomethyl-2-thienylacetamido)penicillanic acid pivaloyloxymethyl ester

In a manner similar to Example 9, but replacing sodium 2-(1-methoxycarbonyl-1-propen-2-ylaminomethyl)-3-thienylacetate with sodium 3-(1-methoxycarbonyl-1-propen-2-ylaminomethyl)-2-thienylacetate, the desired product is prepared.

EXAMPLE 11

Starting with the appropriate 6-aminopenicillanic acid, 1-(alkanoyloxy)alkyl ester and requisite sodium 1-methoxycarbonyl-1-propen-2-ylaminomethyl-thienylacetate and employing the procedure of Example 9, the following compounds are synthesized:
  6-(2-aminomethyl-3-thienylacetamido)penicillanic acid, acetoxymethyl ester;
  6-(2-aminomethyl-3-thienylacetamido)penicillanic acid, propionoyloxymethyl ester;
  6-(2-aminomethyl-3-thienylacetamido)penicillanic acid, 1-acetoxyethyl ester;
  6-(2-aminomethyl-3-thienylacetamido)penicillanic acid, butyryloxymethyl ester;
  6-(2-aminomethyl-3-thienylacetamido)penicillanic acid, isobutyryloxymethyl ester;
  6-(2-aminomethyl-3-thienylacetamido)penicillanic acid, 1-isovaleryloxyethyl ester;
  6-(2-aminomethyl-3-thienylacetamido)penicillanic acid, hexanoyloxymethyl ester;
  6-(2-aminomethyl-3-thienylacetamido)penicillanic acid, 1-valeryloxyethyl ester;
  6-(3-aminomethyl-2-thienylacetamido)penicillanic acid, acetoxymethyl ester;
  6-(3-aminomethyl-2-thienylacetamido)penicillanic acid, 1-acetoxyethyl ester;
  6-(3-aminomethyl-2-thienylacetamido)penicillanic acid, propionoyloxymethyl ester;
  6-(3-aminomethyl-2-thienylacetamido)penicillanic acid, butyryloxymethyl ester;
  6-(3-aminomethyl-2-thienylacetamido)penicillanic acid, isobutyryloxymethyl ester;
  6-(3-aminomethyl-2-thienylacetamido)penicillanic acid, isovaleryloxymethyl ester;
  6-(3-aminomethyl-2-thienylacetamido)penicillanic acid, hexanoyloxymethyl ester; and
  6-(3-aminomethyl-2-thienylacetamido)penicillanic acid, 1-valeryloxyethyl ester.

EXAMPLE 12

6-aminomethyl-3-thienylacetamido)penicillanic acid, phthalidyl ester

To a mixture of 8.7 g. (0.03 mole) of sodium 2-(1-methoxycarbonyl-1-propen-2-ylaminomethyl)-3-thienylacetate and 33 drops of N-methylmorpholine in 65 ml. of ethyl acetate under a nitrogen atmosphere and cooled in a dry-ice/chloroform bath is added dropwise with stirring 3.2 g. (0.03 mole) of ethyl chloroformate. After stirring in the cold for 30 min., 10.4 g. (0.03 mole) of 6-aminopenicillanic acid, phthalidyl ester in 65 ml. of ethyl acetate is added to the reaction mixture and the stirring continued for an additional 3.0 hrs.

While maintaining cooling conditions, 0–5° C., the mixture is quenched with 150 ml. of water and the pH adjusted to 1.5 with 6N hydrochloric acid The mixture is subsequently allowed to stir for 25 min. and the pH raised to 7.5–8.0 using 1N aqueous sodium hydroxide. The organic layer is separated and the aqueous extracted several times with fresh ethyl acetate. The extracts are combined, dried over sodium sulfate and concentrated under reduced pressure to provide the desired product.

EXAMPLE 13

6-(3-aminomethyl-2-thienylacetamido)penicillanic acid, phthalidyl ester

The procedure of Example 12 is repeated, substituting sodium 3-(1-methoxycarbonyl-1-propen-2-ylaminomethyl)-2-thienylacetate for sodium 2-(1-methoxycarbonyl-1-propen-2-ylaminomethyl)-3-thienylacetate to provide the desired product in moderate yield.

EXAMPLE 14

6-(2-aminomethylphenylacetamido)penicillanic acid sodium salt

To a solution of 700 mg. of 6-(2-aminomethylphenylacetamido)penicillanic acid in 7 ml. of dioxane and 40 ml. of water cooled to 10° C. is added 160 mg. (19 m moles) of sodium bicarbonate dissolved in 10 ml. of water. The solution is allowed to sit for 10 min., dialyzed for 30 min., and the filtrate freeze-dried. The resulting solid product is slurried in 40 ml. of chloroform, filtered and dried in vacuo.

In a similar manner, starting with a suitable base, the corresponding potassium, calcium, magnesium and other pharmaceutically acceptable metal salts of 6-(2-aminomethylphenylacetamido)penicillanic acid and the herein described penicillins are prepared.

EXAMPLE 15

6-(2-aminoethyl-3-thienylacetamido)penicillanic acid triethylamine salt

A slurry of 1.4 g. (3.8 m moles) of 6-(2-aminomethyl-3-thienylacetamido)penicillanic acid in 20 ml. of water is treated with 0.5 ml. (3.8 m moles) of triethylamine. After stirring for 5 min., a small amount of insolubles are filtered, and the filtrate is freeze-dried to provide the desired salt.

In a similar manner, the ammonium salt and pharmaceutically acceptable salts derived from organic amines for the above-described penicillin and the other herein described penicillins are prepared.

EXAMPLE 16

6-(2-aminomethylphenylacetamido)penicillanic acid, pivaloyloxymethyl ester hydrochloride To 1.4 g. (3 m moles) of 6-(2-aminomethylphenylacetamido)penicillanic acid, pivaloyloxymethyl ester in 15 ml. of water and 10 ml. of tetrahydrofuran, cooled in an ice bath, is added 3 ml. of 1N hydrochloric acid (3 m moles) and the solution freeze dried. The product is triturated with acetone and filtered.

EXAMPLE 17

6-(2-aminomethyl-4-hydroxyphenylacetamido)penicillanic acid phthalidyl ester citrate In a manner similar to Example 16, 1.5 g. (3 m moles) of 6-(2-aminomethyl-4-hydroxyphenylacetamido)penicillanic acid, phthalidyl ester in 10 ml. of water and 15 ml. of tetrahydrofuran is treated with 576 mg. (3 m moles) of citric acid in one ml. of water to yield the desired product.

By a similar procedure, the compounds of the present invention are converted to their pharmaceutically acceptable salts.

EXAMPLE 18

A tablet base is prepared by blending the following ingredients in the proportion by weight indicated:

| | | |
|---|---|---|
| Sucrose, U.S.P. | 80.0 | |
| Tapioca starch | 12.5 | |
| Magnesium stearate | 7.5 | |

Sufficient 6-(2-aminomethylphenylacetamido)-penicillanic acid sodium salt is blended into the base to provide tablets containing 100, 250 and 500 mg. of active ingredient.

EXAMPLE 19

A suspension of 6-(2-aminomethyl-phenylacetamido)penicillanic acid hydrochloride is prepared with the following composition:

| | | |
|---|---|---|
| Penicillin compound | 31.42 | g. |
| 70% Aqueous sorbitol | 714.29 | g. |
| Glycerine, U.S.P. | 185.35 | g. |
| Gum acacia (10% solution) | 100.00 | ml. |
| Polyvinyl pyrrolidone | 0.50 | g. |
| Propyl parahydroxybenzoate | 0.072 | g. |
| Distilled water to make 1 liter | 0.094 | g. |

Various sweetening and flavoring agents may be added to this suspension, as well as acceptable coloring. The suspension contains approximately mg. of penicillin compound per milliliter.

EXAMPLE 20

Capsules containing 100, 250 and 500 mg. of active ingredient are prepared by blending sufficient 6-(2-aminomethyl-4-hydroxyphenylacetamido)-penicillanic acid, pivaloyloxymethyl ester hydrochloride in the following mixture (proportions given in parts by weight):

| | |
|---|---|
| Calcium carbonate, U.S.P. | 17.5 |
| Dicalcium phosphate | 18.9 |
| Magnesium trisilicate | 4.2 |
| Lactose, U.S.P. | 6.2 |
| Potato starch | 5.2 |
| Magnesium stearate | 1.0 |

Following the blending, the indicated capsules are prepared.

EXAMPLE 21

A parenteral form of 6-(2-aminomethyl-3-thienylacetamido)penicillanic acid sodium salt is prepared by dissolving an intimate mixture of the penicillin compound and sodium citrate (4% by weight) in sufficient polyethylene glycol 200 such that the final concentration of the penicillin compound is 250 mg. of active ingredient per milliliter. The resulting solution is sterilized by filtration and sterilely stoppered in vials.

In like manner, formulations of the products of this invention are made.

PREPARATION A

Aminomethylarylacetic acids 1. 2-Aminomethylphenylacetic Acid
2-Aminomethylphenylacetic acid is synthesized by the method as taught in U.S. Pat. Nos. 3,796,716 and/or 3,796,717.

2. 2-aminomethyl-4-hydroxyphenylacetic acid
Following the procedure in Netherlands Pat. No. 7312062, the desired intermediate is prepared.

3. 2-aminomethyl-3-thienylacetic acid
a. N-acetyl-2-aminomethyl-3-methylthiophene
2-Aminomethyl-3-methylthiophene (H. D. Hartough, et al., J. Am. Chem. Soc., 70, 4018 [1948]) is dissolved in pyridine and treated with excess acetic anhydride overnight. The solvent is removed under pressure, the residue dissolved in ethyl acetate and washed with dilute hydrochloric acid and sodium bicarbonate solution. The organic extract is dried over magnesium sulfate and evaporated to yield the desired compound.

b. N-Acetyl-2-aminomethyl-3-bromomethylthiophene
N-Acetyl-2-aminomethyl-3-methylthiophene is dissolved in carbon tetrachloride and treated with an equimolar amount of N-bromosuccinimide and a catalytic amount of dibenzoyl peroxide. The mixture is heated to reflux for 3 hours while irradiating with a 250 watt light. The mixture is cooled and the precipitated succinimide removed by filtration. The filtrate is washed with saturated sodium bisulphite solution, dried over magnesium sulfate and evaporated to yield the title compound.

c. N-acetyl-2-aminomethyl-3-cyanomethylthiophene
N-acetyl-2-aminomethyl-3-bromomethylthiophene is dissolved in dry dimethylformamide and one equivalent of sodium cyanide is added. The mixture is stirred overnight, the sodium bromide removed by filtration and the filtrate evaporated yielding the desired product.

d. (2-aminomethyl-3-thienyl)acetic acid
A suspension of N-acetyl-2-aminomethyl-3-cyanomethylthiophene in concentrated hydrochloric acid is stirred under reflux for 3 hours by which time a homogeneous solution is formed. The solution is evaporated to dryness, the resulting solid is dissolved in the minimum of water and the pH adjusted to 5.5 with sodium hydroxide solution. The precipitate of (2-aminomethyl-3-thienyl)acetic acid is collected by filtration.

4. 3-aminomethyl-2-thienylacetic acid
a. 2-thienylacetamide
2-thienylacetic acid is dissolved in methylene chloride and treated with a 25% excess of thionyl chloride. The mixture is allowed to stand at room temperature for 2 days and evaporated yielding a dark brown mobile liquid. This is dissolved in methylene chloride and gaseous ammonia bubbled into the mixture for 4 hours. The mixture is allowed to stand at room temperature overnight and partitioned between ethyl acetate and water. The ethyl acetate layer is dried over sodium sulfate and evaporated yielding a pale brown solid which is crystallized from water to yield the desired product, m.p. 146–149° C. (lit. 147° C., Crowe et al., J. Org. Chem., 15, 81–8 [1950]).

b. N-Hydroxymethyl-2-thienylacetamide
A mixture of 2-thienylacetamide, formaldehyde solution (37%, 1 equivalent) and a catalytic amount of potassium carbonate is warmed on a steam bath until a homogeneous solution is obtained. The solution is cooled to 0° C. overnight and the resulting solid collected by filtration.

c. 3-aminomethyl-2-thienylacetic acid lactam

Finely powdered N-hydroxymethyl-2-thienylacetamide is added portionwise at 10°–15° C. to concentrated sulfuric acid with vigorous stirring. The mixture is stirred for 5 days and then poured onto ice. The mixture is neutralized with potassium carbonate and extracted thoroughly with ethyl acetate. The organic phase is dried and evaporated yielding the desired lactam.

d. 3-aminomethyl-2-thienylacetic acid

A suspension of 3-aminomethyl-2-thienylacetic acid lactam in concentrated hydrochloric acid is heated to reflux for 3 hours. The mixture is cooled, evaporated and the resultant solid dissolved in the minimum amount of water. The pH is adjusted to 5.5 with sodium hydroxide solution and the precipitated amino acid collected by filtration.

PREPARATION B

1-Methoxycarbonyl-1-propen-2-ylaminomethyl Substituted Arylacetic Acids

The amino moiety of the aminomethyl substituted arylacetic acids is blocked by the method as taught in U.S. Pat. No. 3,813,376, employing the requisite aminomethyl arylacetic acid and methyl acetoacetate.

What is claimed is:

1. A compound selected from the group consisting of:

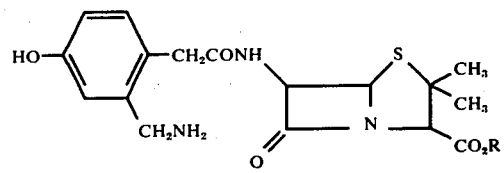

and the pharmaceutically acceptable salts thereof wherein R is selected from the group consisting of hydrogen, 1-(alkanoyloxy)alkyl, said alkanoyl having 2 to 8 carbon atoms and said alkyl having from 1 to 3 carbon atoms, and phthalidyl.

2. A compound of claim 1 wherein R is hydrogen.

3. A compound of claim 1 wherein R is said 1-(alkanoyloxy)alkyl.

4. The compound of claim 3 wherein R is pivaloyloxymethyl and X is hydroxyl.

5. A compound of claim 1 wherein R is phthalidyl.

6. The compound of claim 5 wherein X is hydroxy.

* * * * *